United States Patent
Mirza et al.

(10) Patent No.: US 12,287,306 B2
(45) Date of Patent: Apr. 29, 2025

(54) SYSTEM AND METHOD FOR DETERMINING AN AMBIENT CONCENTRATION OF COMPOSITIONS FOR BATHROOM CLEANING

(71) Applicant: 7-Eleven, Inc., Irving, TX (US)

(72) Inventors: Shahmeer Ali Mirza, Celina, TX (US); John Robert Keller, Plano, TX (US); Matthew O'Daniel Redmond, Denton, TX (US)

(73) Assignee: 7-ELEVEN, INC., Irving, TX (US)

( * ) Notice: Subject to any disclaimer, the term of this patent is extended or adjusted under 35 U.S.C. 154(b) by 638 days.

(21) Appl. No.: 17/455,775

(22) Filed: Nov. 19, 2021

(65) Prior Publication Data
US 2023/0160848 A1    May 25, 2023

(51) Int. Cl.
*G01N 27/404*    (2006.01)
*G01N 33/00*    (2006.01)

(52) U.S. Cl.
CPC ..... *G01N 27/4045* (2013.01); *G01N 33/0047* (2013.01); *G01N 33/0068* (2024.05)

(58) Field of Classification Search
CPC .................................................. G01N 27/4045
USPC ....................................................... 73/31.05
See application file for complete search history.

(56) References Cited

U.S. PATENT DOCUMENTS

| | | | |
|---|---|---|---|
| 9,116,137 B1 * | 8/2015 | Gettings | G01N 33/00 |
| 2017/0062287 A1 * | 3/2017 | Kim | H01L 21/67086 |
| 2020/0090132 A1 * | 3/2020 | Bender | G06F 16/337 |
| 2021/0088488 A1 * | 3/2021 | Egli | G01N 33/0006 |
| 2022/0067093 A1 * | 3/2022 | Su | G01N 33/0001 |
| 2022/0205974 A1 * | 6/2022 | Abe | G01N 33/0062 |

OTHER PUBLICATIONS

Keller, J. R. et al., "System and Method for Diagnostic Analysis of a Toilet Over Time Intervals," U.S. Appl. No. 17/455,716, filed Nov. 19, 2021, 43 pages.

* cited by examiner

*Primary Examiner* — Walter L Lindsay, Jr.
*Assistant Examiner* — Philip T Fadul
(74) *Attorney, Agent, or Firm* — Baker Botts L.L.P.

(57) ABSTRACT

A system for determining an ambient concentration of compositions for bathroom cleaning comprises a processor operable to receive a concentration measurement from a sensor over a network within a first period of time. The processor is operable to compare the received concentration measurement to a first threshold and to a second threshold greater than the first threshold. The processor is operable to instruct a memory communicatively coupled to the processor to store an indication that a bathroom was cleaned in response to a determination that the received concentration measurement is greater than the first threshold and less than the second threshold. The processor is operable to send an alert for display on a user device indicating either that the sensor has been tampered or that a spill event has occurred in response to a determination that the received concentration measurement is greater than the second threshold.

20 Claims, 3 Drawing Sheets

SYSTEM AND METHOD FOR DETERMINING AN AMBIENT CONCENTRATION OF COMPOSITIONS FOR BATHROOM CLEANING

TECHNICAL FIELD

The present disclosure relates generally to sensors. More particularly, the present disclosure relates to a system and method for determining an ambient concentration of compositions for bathroom cleaning.

BACKGROUND

A plurality of parameters can be correlated to the cleanliness of a bathroom. An entity managing the bathroom is not able to measure certain parameters and determine how each parameter affects the cleanliness of the bathroom.

SUMMARY

Existing systems and methods used for monitoring a toilet and the cleanliness of a bathroom suffer from disadvantages. For example, this disclosure recognizes that existing systems do not employ one or more sensors to measure a parameter related to the bathroom. The existing systems and methods are not able to determine when the bathroom has been cleaned or requires cleaning based on measurements from the one or more sensors.

The disclosed system provides several practical applications and technical advantages that overcome the previously discussed technical problems. For example, the disclosed system provides a practical application by employing an alerting system that is configured to collect information about the number of instances of a decrease in water in the toilet tank and the number of instances the door transitions from an open and closed position, determine whether certain conditions are met or if thresholds are exceeded, and to alert a user to take an action within a given period of time, such as cleaning the bathroom. In this example, a distance sensor may be used to determine iterative distance measurements of water level within the toilet tank over a period of time. Those distance measurements may be compared to a threshold over a period of time. Those distance measurements may further be used to calculate a ratio of the number of instances of a decrease in water level in the toilet tank to the number of instances where a user opens the door to the bathroom. The alerting system may transmit the alert to a user device in order to prompt a user to clean the toilet associated with the toilet tank or to clean the bathroom if certain conditions are met.

The alerting system monitors how many times a toilet in a bathroom has been flushed over a period of time in order to schedule a cleaning of the toilet. For example, users may utilize the toilet during an interaction with an entity. The entity may be a store offering goods for purchase by the users. In this example, the entity may be a convenience store where the users may utilize the toilet before or after purchasing goods from the entity (i.e., snacks, beverages, etc.). The convenience store may have a schedule for cleaning the bathroom, such as once per day. Over time, the bathroom may get increasingly dirty, and the scheduled cleaning may be ineffective in maintaining a clean bathroom for the users. To maintain a clean bathroom, the alerting system identifies when to alert the entity that the bathroom needs cleaning based on the number of times a toilet has been flushed. There may be an inverse relationship between the number of times a toilet has been flushed and cleanliness of the bathroom. For example, as the number of times the toilet flushes increases, the cleanliness of the bathroom decreases.

Further, the alerting system monitors how many times a door to the bathroom has opened and closed over a period of time in order to schedule a cleaning for the toilet. For example, users may open and close a door each time before utilizing the bathroom. Once in the bathroom, the user may utilize the toilet. If the toilet is not working or is too dirty for use, the user may exit the bathroom through the door. The alerting system identifies this event by monitoring the door and identifying that the toilet was not flushed while the user was in the bathroom. The entity managing the bathroom (i.e., the convenience store) determines that the toilet is not working or is too dirty for use when the alerting system determines that the number of times the toilet has flushed in relation to the number of times the door has been opened and closed is below a certain ratio.

In an embodiment, a system for diagnostic analysis of a bathroom over time intervals comprises a sensor disposed within a toilet tank. The sensor comprises a laser diode, a photodetector, and a first processor. The laser diode is operable to produce a laser beam pulse that travels towards a water level within the toilet tank, wherein the laser beam pulse is reflected back to the sensor. The photodetector is operable to receive the reflected laser beam pulse. The first processor is communicatively coupled to the laser diode and to the photodetector. The first processor is configured to determine a distance measurement based on a difference in time between production of the laser beam pulse and reception of the reflected laser beam pulse and to transmit the distance measurement across a network. The system further comprises a computer system communicatively coupled to the sensor using the network, comprising a memory and a second processor. The memory is operable to store door information comprising a number of instances wherein a door changes from a first position to a second position within a period of time, store a threshold ratio of a number of instances of a decrease in the water level to the number of instances wherein the door changes from the first position to the second position, and store a setpoint corresponding to an initial water level in the toilet tank. The second processor is operably coupled to the memory and configured to receive the distance measurement from the network. The second processor is further configured to determine an instance of the decrease in the water level in the toilet tank based on a comparison of the received distance measurement to the setpoint and determine a plurality of instances of the decrease in the water level within the period of time. The second processor is further configured to calculate a ratio of the determined number of the plurality of instances of the decrease in the water level to the number of instances wherein the door changes from the first position to the second position based on the door information stored in the memory. The second processor is further configured to compare the calculated ratio to the threshold ratio and to send an alert for display on a user device when the calculated ratio is less than the threshold ratio.

The disclosed system provides further practical applications and technical advantages by employing an alerting system that is configured to collect information about the concentration of one or more compounds, such as volatile organic compounds (VOC), present in the bathroom, determine whether certain conditions are met or if thresholds are exceeded, and to alert a user to take an action within a given period of time, such as cleaning the bathroom.

The alerting system determines the concentration of one or more VOCs within the ambient environment of the bathroom in order to monitor cleaning of the bathroom. For example, the entity managing the bathroom (i.e., the convenience store) may have a schedule for cleaning the bathroom, such as once per twelve hours. Someone associated with the entity, such as an employee, may be too busy performing other tasks to comply with the cleaning schedule. To monitor the cleaning of the bathroom for compliance, the alerting system may register an event associated with cleaning the bathroom based on different threshold values for various cleaning solutions. However, the employee may forget to clean the bathroom, may spill chemicals in an attempt to clean the bathroom, perform a cursory cleaning, or try to deceive the system in order to perform other tasks.

In another embodiment, a system for determining an ambient concentration of a volatile organic compound comprises a sensor disposed proximate to an exhaust fan operable to receive an airflow from the exhaust fan. The sensor comprises a light source, a pair of electrodes, and a first processor. The light source is operable to produce a light configured to ionize one or more molecules of the volatile organic compound present in the airflow. The pair of electrodes is operable to receive the ionized one or more molecules and to generate an electrical current proportional to a concentration of the ionized one or more molecules. The first processor is communicatively coupled to the pair of electrodes and is configured to determine a concentration measurement for the volatile organic compound based at least in part upon the electrical current generated by the pair of electrodes and to transmit the concentration measurement across a network. The system further comprises a computer system communicatively coupled to the sensor, comprising a memory and second processor. The memory is operable to store a first threshold for the concentration measurement associated with an event of cleaning a bathroom and store a second threshold for the concentration measurement, wherein the second threshold is greater than the first threshold. The second processor is configured to receive the concentration measurement from the network within a first period of time and to compare the received concentration measurement to the first threshold. The second processor is further configured to compare the received concentration measurement to the second threshold and to instruct the memory to store an indication that the bathroom was cleaned in response to a determination that the received concentration measurement is greater than the first threshold and less than the second threshold.

A practical application is provided for identifying a current state of cleanliness for the bathroom and maintaining an optimal state of cleanliness based on the measurements provided by the sensors. For example, during a period of time, the alerting system receives information from various sensors associated with the bathroom. The alerting system can autonomously determine whether one or more conditions have been met before generating and transmitting and alert prompting an action be taken. The alerting system can maintain compliance for scheduled cleaning and identify when a toilet may need to be serviced based on received information and threshold numbers or ratios.

Certain embodiments of the present disclosure may include some, all, or none of these advantages. These advantages and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

This disclosure provides solutions to the aforementioned and other problems of previous technology through an automatic alerting process for diagnostic analysis of a toilet over time intervals. The disclosure further provides an automatic alerting process for determining an ambient concentration of compositions for bathroom cleaning.

Automatic Alerting System

Figure 1:
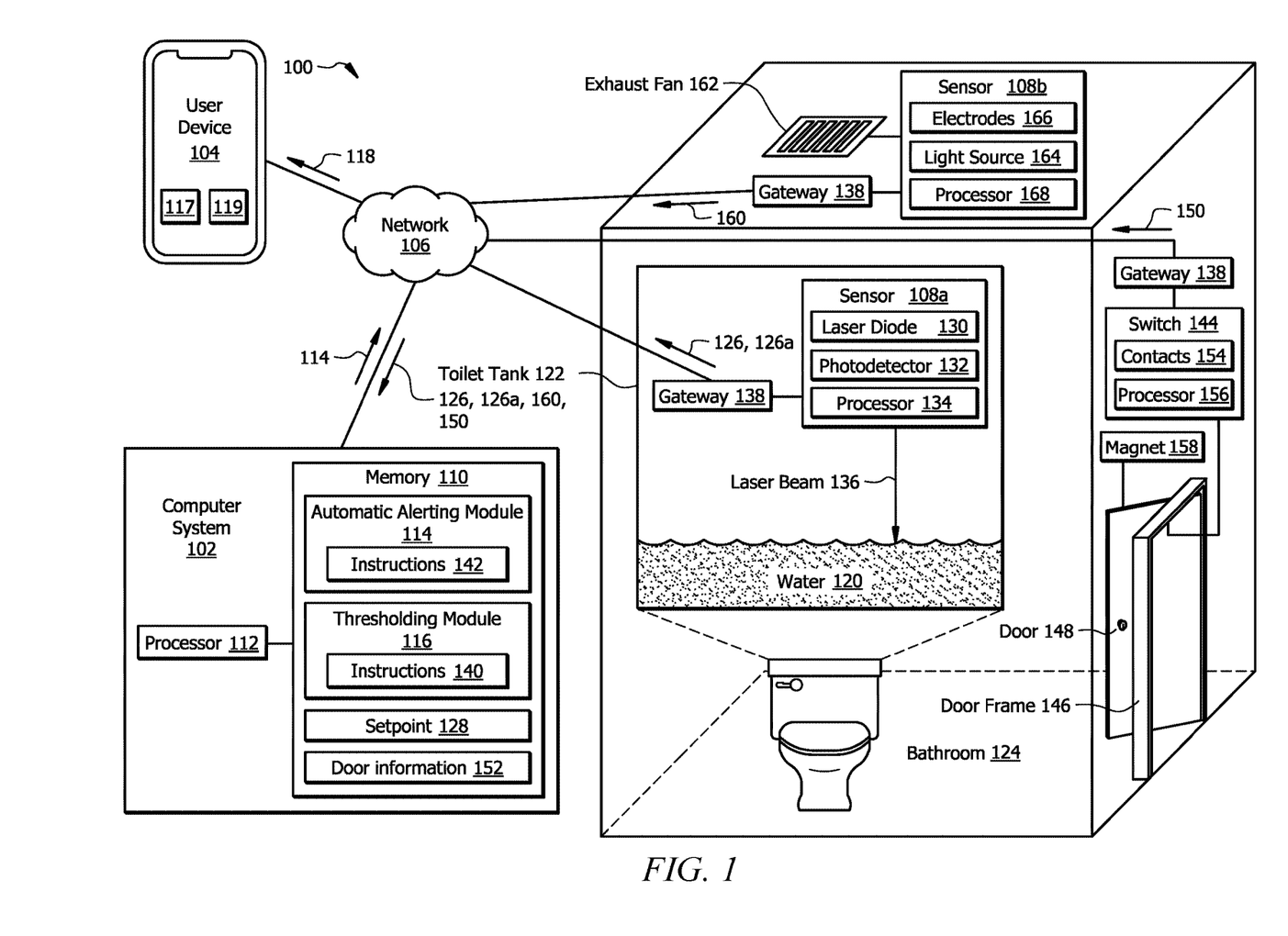
FIG. 1 is a schematic diagram of an example automatic alerting system.

FIG. 1 illustrates a schematic diagram of an example automatic alerting system 100. As illustrated in FIG. 1, the automatic alerting system 100 includes a computer system 102, a user device 104, a network 106, and one or more sensors 108. Computer system 102 is communicatively coupled to user device 104 and the one or more sensors 108 via the network 106 using any appropriate wired or wireless telecommunication technology.

Computer system 102 may be any appropriate computing system in any suitable physical form. As example and not by way of limitation, computer system 102 may be an embedded computer system, a system-on-chip (SOC), a single-board computer system (SBC) (such as, for example, a computer-on-module (COM) or system-on-module (SOM)), a desktop computer system, a laptop or notebook computer system, a mainframe, a mesh of computer systems, a mobile telephone, a personal digital assistant (PDA), a server, a tablet computer system, an augmented/virtual reality device, or a combination of two or more of these. Where appropriate, computer system 102 may include one or more computer systems 102; be unitary or distributed; span multiple locations; span multiple machines; span multiple data centers; or reside in a cloud, which may include one or more cloud components in one or more networks. Where appropriate, one or more computer systems 102 may perform without substantial spatial or temporal limitation one or more steps of one or more methods described or illustrated herein. As an example and not by way of limitation, one or more computer systems 102 may perform in real time or in batch mode one or more steps of one or more methods described or illustrated herein. One or more computer systems 102 may perform at different times or at different locations one or more steps of one or more methods described or illustrated herein, where appropriate. The computer system 102 may include a memory 110 operable to store information and/or provide access to application(s), wherein the memory 110 includes software instructions that, when executed by a processor 112, cause the computer system 102 to perform one or more functions described below. Computer system 102 may be physically located within the same physical building in which one or more sensors 108 are located, or physically located at a location remote from the physical building in which one or more sensors 108 are located. For example, in certain embodiments, computer system 102 may be located in one or more remote servers (e.g., in the cloud). Details of the operations of the computer system 102 are described in conjunction with FIGS. 2-3.

Processor 112 is any electronic circuitry, including, but not limited to a microprocessor, an application specific integrated circuits (ASIC), an application specific instruction set processor (ASIP), and/or a state machine, that communicatively couples to memory 110 and controls the operation of computer system 102. Processor 112 may be 8-bit, 16-bit, 32-bit, 64-bit or of any other suitable architecture. Processor 112 may include an arithmetic logic unit (ALU) for performing arithmetic and logic operations, processor registers that supply operands to the ALU and store the results of ALU operations, and a control unit that fetches instructions from memory and executes them by directing the coordinated operations of the ALU, registers and other components. Processor 112 may include other hardware that operates software to control and process information. Processor 112 executes software stored in memory to perform any of the functions described herein. Processor 112 controls the operation and administration of computer system 102 by processing information received from one or more sensors 108, network 106, user device 104, and memory 110. Processor 112 may be a programmable logic device, a microcontroller, a microprocessor, any suitable processing device, or any suitable combination of the preceding. Processor 112 is not limited to a single processing device and may encompass multiple processing devices.

Memory 110 may store, either permanently or temporarily, data (such as distance measurements 126 or concentration measurements 160 described further below), user preferences, business rules, operational software such as automatic alerting module 114 (described further below) and thresholding module 116 (described further below), or other information for processor 112. Memory 110 may include any one or a combination of volatile or non-volatile local or remote devices suitable for storing information. For example, memory 110 may include random access memory (RAM), read only memory (ROM), magnetic storage devices, optical storage devices, or any other suitable information storage device or a combination of these devices.

User device 104 is any appropriate device for communicating with components of computer system 102 over network 106. For example, user device 104 may be a handheld computing device such as a smartphone, wearable computer glasses, a smartwatch, a tablet computer, a laptop computer, and the like. User device 104 may include an electronic display, a processor such as processor 112, and memory such as memory 110. The electronic display of user device 104 may display an alert 118 (described further below) that is provided by computer system 102. For example, in certain embodiments, user device 104 may generate a pop-up message that includes the alert 118, and automatically display the pop-up message on a screen of user device 104. In some embodiments, user device 104 may generate a sound and/or vibration in response to receiving alert 118. In certain embodiments, user device 104 may display a graphical user interface (GUI) on a screen of user device 104 within which the alert 118 may be displayed. In further examples, user device 104 may receive alert 118 through an email and/or text message. The alert 118 may indicate that a condition has been met and may signal for an event to occur. After receiving the alert 118, a user associated with the user device 104 may proceed to take action according to the alert 118.

In certain embodiments, user device 104 may receive measurements made by one or more sensors 108 and use the measurements to monitor a cleaning schedule of a bathroom and to determine whether to clean the bathroom or a toilet located in the bathroom. In these embodiments, the one or more sensors 108 may directly communicate with the user device 104 instead of with the computer device 102. For example, in such embodiments, a memory 117 of user device 104 may include instructions (e.g., instructions 140 and/or 142 described in detail below) that, when executed by a processor 119 of user device 104, enable the device to determine, based on the received measurements, whether to clean the bathroom or a toilet located in the bathroom, or whether a cleaning has occurred in view of the cleaning schedule. For example, instructions stored in memory 117 may indicate that: a number of times a toilet has flushed exceeds a threshold, a ratio of the number of times the toilet has flushed to a number of times a door to the bathroom has opened is less than a threshold ratio, and a concentration of a volatile organic compound present in the bathroom exceeds a threshold. In response to any one of these events, user device 104 may automatically generate and display an alert for a user associated with user device 104.

Network 106 allows communication between and amongst the various components of system 100. For example, computer system 102, user device 104, and one or more sensors 108 may communicate via network 106. This disclosure contemplates network 106 being any suitable network operable to facilitate communication between the components of system 100. Network 106 may include any interconnecting system capable of transmitting audio, video, signals, data, messages, or any combination of the preceding. Network 106 may include all or a portion of a local area network (LAN), a wide area network (WAN), an overlay network, a software-defined network (SDN), a virtual private network (VPN), a packet data network (e.g., the Internet), a mobile telephone network (e.g., cellular networks, such as 4G or 5G), a Plain Old Telephone (POT) network, a wireless data network (e.g., WiFi, WiGig, WiMax, etc.), a Long Term Evolution (LTE) network, a Universal Mobile Telecommunications System (UMTS) network, a peer-to-peer (P2P) network, a Bluetooth network, a Near Field Communication (NFC) network, a Zigbee network, and/or any other suitable network, operable to facilitate communication between the components.

Example Automatic Alerting System for Diagnostic Analysis of a Toilet Over Time Intervals The automatic alerting system 100 may be implemented to monitor how many times a toilet in a bathroom has been flushed over a period of time in order to schedule a cleaning of the toilet. For example, users may utilize the toilet during an interaction with an entity. The entity may be a store offering goods for purchase by the users. In this example, the entity may be a convenience store where the users may utilize the toilet before or after purchasing goods from the entity (i.e., snacks, beverages, etc.). The convenience store may have a schedule for cleaning the bathroom, such as once per day. Over time, the bathroom may get increasingly dirty, and the scheduled cleaning may be ineffective in maintaining a clean bathroom for the users. To maintain a clean bathroom, the automatic alerting system 100 may identify when to alert the entity that the bathroom needs cleaning based on the number of times a toilet has been flushed. There may be an inverse relationship between the number of times a toilet has been flushed and cleanliness of the bathroom. For example, as the number of times the toilet flushes increases, the cleanliness of the bathroom decreases.

In one or more embodiments, this process uses the sensor 108a to determine a distance to a level of water 120 contained within a toilet tank 122 disposed in a bathroom 124. The toilet tank 122 may be a structure serving as a containment chamber of any suitable toilet operable to receive water 120 from an external source and contain the water 120 until a user actuates the toilet to allow for the water 120 to flow out of the toilet tank 122 (i.e., an event of a flush). As illustrated, computer system 102 may receive data in the form of distance measurements 120 that are generated by sensor 108*a*. The computer system 102 further generates the alert 118 for display on the user device 104 based on comparing the distance measurements 126 to a setpoint 128 (described further below) stored in the memory 110. In general, the computer system 102 may perform an alerting process based on the received distance measurements 126.

The sensor 108*a* is any appropriate device for sensing or measuring the physical distance to an object. For example, sensor 108*a* may be a time of flight (ToF) sensor that utilizes a laser to produce a beam of infrared light that is bounced off an object and returned to the sensor 108*a* in order to measure distance to the object. Sensor 108*a* may include a laser diode 130, a photodetector 132, and a sensor processor 134. In a particular embodiment, the laser diode 130 may produce a laser beam 136 that travels towards a level of water 120, wherein the laser beam 136 is reflected off of the water 120 to travel back to the sensor 108*a*. The laser diode 130 may produce pulses of laser beams 130 at a pre-determined frequency. The photodetector 132 may be any appropriate device operable to receive each reflected laser beam 136. In one or more embodiments, the sensor processor 134 may be communicatively coupled to the laser diode 130 and to the photodetector 132. The sensor processor 134 may determine a distance measurement 126 based on a difference in time between production of the laser beam 136 by the laser diode 130 and reception of the reflected laser beam 136 by the photodetector 132. The sensor processor 134 may further transmit each distance measurement 126 across the network 106.

In general, sensor 108*a* provides the distance measurement 126 to computer system 102. Distance measurement 126 may comprise any appropriate distance value (e.g., inches or millimeters). In some embodiments, distance measurement 126 is provided automatically by sensor 108*a* at periodic intervals (e.g., every five minutes). In other embodiments, distance measurement 126 is provided by sensor 108*a* when requested by computer system 102.

In some embodiments, sensor 108*a* may operate as an Internet-of-Things (IoT) sensor. In general, IoT describes a network of physical objects that are embedded with sensors, software, and other technologies for the purpose of connecting and exchanging data with other devices and systems over the Internet, or any suitable network. In embodiments where sensor 108*a* is an IoT sensor, automatic alerting system 100 may include a gateway 138 for communicating with each one of sensors 108. Gateway 138 may be any appropriate IoT gateway, computer system, or electronic device that is capable of wirelessly communicating with sensor 108*a* using any appropriate IoT communications protocol. Without limitations, the IoT communications protocol may include message queuing telemetry transport (MQTT), constrained application protocol (CoAP), advanced message queuing protocol (AMQP), data-distribution service (DDS), Zigbee, Z-Wave, lightweight machine-to-machine (LwM2M), or any combinations thereof. For example, sensor 108*a* may wirelessly transmit distance measurement 126 to gateway 138, and gateway 138 may in turn send distance measurement 126 to computer system 102 via network 106. In other embodiments, the sensor 108*a* may not be an IoT sensor. In embodiments where the sensor 108*a* is not operable as an IoT sensor, sensor 108*a* may transmit distance measurement 126 directly to computer system 102 via network 106 (i.e., without utilizing gateway 138).

For example, in a particular embodiment, the sensor 108*a* may be disposed or mounted within the toilet tank 122 above the level of water 120. The computer system 102 may calibrate the sensor 108*a* to provide measurements relative to the toilet tank 122 by instructing the sensor 108*a* to perform a first distance measurement 126*a* to determine a distance from the level of water 120 to the sensor 108*a* at an initial level (i.e., when the toilet tank 122 has not been actuated to flush the water 120). The sensor 108*a* may transmit the first distance measurement 126*a* to the computer system 102 for storage as the setpoint 128. The computer system 102 may determine an instance of a decrease in the level of water 120 (for example, an event associated with flushing the toilet tank 122) based on a comparison between a received distance measurement 126 and the setpoint 128. For example, if the received distance measurement 126 is greater than the setpoint 128, the computer system 102 determines that an event associated with flushing the toilet tank 122 has occurred. In this example, the greater value of the received distance measurement 126 indicates that there was a decrease in the level of water 120 relative to the setpoint 128. As a user flushes the toilet, the level of water 120 decreases in the toilet tank 122 and flows further down through the toilet.

During operation, the sensor 108*a* may determine a plurality of distance measurements 126 from the level of the water 120 to the sensor 108*a* (a "water level"), wherein the computer system 102 may receive the plurality of distance measurements 126 transmitted over the network 106. The computer system 102 may determine a plurality of instances of the decrease in the level of water 120 based on the received plurality of distance measurements 126. In embodiments, the determined plurality of instances of the decrease in the level of water 120 may be compared to a threshold number set by the thresholding module 116. For example, the threshold number represents the allowable number of flushes for a toilet before the entity cleans the toilet. The threshold number may be any suitable value (for example, 5, 10, 15, etc.). In an example, if the determined plurality of instances of the decrease in the level of water 120 is six and the threshold number is five, the computer system 102 may generate and transmit the alert 118.

Thresholding module 116 represents any suitable set of instructions, logic, or code embodied in a computer-readable storage medium. For example, thresholding module 116 may be embodied in memory 110, a disk, a CD, or a flash drive. In particular embodiments, thresholding module 116 may include thresholding instructions 140 (e.g., a software application) executable by processor 112 to perform one or more of the functions described herein. In general, thresholding instructions 140 may determine the threshold number of instances of the decrease in the level of water 120 for a period of time.

The computer system 102 may transmit the alert 118 to the user device 104 when the determined plurality of instances of the decrease in the level of water 120 is greater than the threshold number. For example, the alert 118 may be generated and transmitted when the computer system 102 determines that a toilet has flushed twenty-one times and the threshold number is twenty during a period of six hours. The alert 118 may indicate that the determined plurality of instances of the decrease in the level of water 120 has exceeded the threshold number within a period of time and prompt an event, such as cleaning the toilet associated with the toilet tank 122. In another example, a toilet may not be working or may be too dirty for use. There may be a determination that the toilet has flushed five times within the first hour of a period of six hours. If a designated time interval is two hours and there is no subsequent flush after that time interval (i.e., after the third hour), the computer system 102 may generate and transmit the alert 118. The alert 118 may indicate that there has been no change in the determined number of the plurality of instances of the decrease in the level of water 120 over a time interval and prompt an event, such as cleaning and/or performing maintenance on the toilet associated with the toilet tank 122. In these examples, the alert 118 may be generated and transmitted via the automatic alerting module 114 of the computer system 102.

Automatic alerting module 114 represents any suitable set of instructions, logic, or code embodied in a computer-readable storage medium. For example, automatic alerting module 114 may be embodied in memory 110, a disk, a CD, or a flash drive. In particular embodiments, automatic alerting module 114 may include alerting instructions 142 (e.g., a software application) executable by processor 112 to perform one or more of the functions described herein. In general, automatic alerting module 114 sends alert 118 for display on user device 104 via network 106. As described, alert 118 is generated by automatic alerting module 114 based, at least in part, on the distance measurements 126 from sensor 108a. The alerting instructions 142 may generate and transmit the alert 118 when the determined plurality of instances of the decrease in the level of water 120 has exceeded the threshold number within a period of time, when there has been no change in the determined number of the plurality of instances of the decrease in the level of water 120 over a time interval, or both.

In another example, the automatic alerting system 100 may be implemented to monitor how many times a door to the bathroom has opened and closed over a period of time in order to schedule a cleaning for the toilet. For example, users may open and close a door each time before utilizing the bathroom. Once in the bathroom, the user may utilize the toilet. If the toilet is not working or is too dirty for use, the user may exit the bathroom through the door without using the toilet. The automatic alerting system 100 may identify this event by monitoring the door and identifying that the toilet was not flushed while the user was in the bathroom. The entity managing the bathroom (i.e., the convenience store) may determine that the toilet is not working or is too dirty for use when the automatic alerting system 100 determines that the number of times the toilet has flushed in relation to the number of times the door has been opened and closed is below a certain ratio.

The automatic alerting system 100 may include any suitable sensors or switches to monitor the opening and closing of a door. In particular embodiments, a switch 144 may be used in conjunction with the sensor 108a to generate the alert 118 to be displayed on the user device 104. For example, in a particular embodiment, the switch 144 may be disposed or coupled to a door frame 146 associated with the bathroom 124. A door 148 may be coupled to the door frame 146 operable to rotate about a side of the door frame 146 between a first position (i.e., closed) and a second position (i.e., open). In certain embodiments, the door 148 and door frame 146 may serve as an entryway into and out of the bathroom 124. In other embodiments, the door 148 and door frame 146 may serve as an entryway into and out of an individual stall within the bathroom 124. The switch 144 may transmit a signal 150 indicating an instance of transition between positions for the door 148 to the computer system 102 for storage as door information 152.

Switch 144 is any appropriate device for determining a condition based on transitioning between positions due to manual operation or in response to a determined parameter. For example, switch 144 may be a reed switch operable to open or close based on proximity to a magnetic field. In other examples, the switch 144 may be a toggle switch, rotary switch, biased switch, slide switch, or an electronic switch. Switch 144 may include a pair of contacts 154 and a switch processor 156. In a particular embodiment, the switch 144 may be coupled to the door frame 146. The pair of contacts 154 may be in a closed position when in proximity to a magnet 158 coupled to the door 148, wherein the pair of contacts 154 transitions from the closed position to an open position as the door 148 changes from the first position to the second position (for example, by rotating along a side of the door frame 146). In one or more embodiments, the switch processor 156 may be communicatively coupled to the pair of contacts 154. The switch processor 156 may determine an instance of transition from the closed position to the open position. The switch processor 156 may further transmit each instance of transition across the network 106. In other embodiments, the switch 144 may be communicatively coupled to a gateway 138, wherein the gateway 138 may send the instance of transition to computer system 102 via network 106.

In an example, the computer system 102 may identify when the toilet is inoperable or is dirty based on a ratio of the number of flushes to the number of times the door 148 opens and closes. For example, if the door opens and closes a certain number of times more than the number of times the toilet flushes, the computer system 102 may identify that the entity operating the bathroom 124 (i.e., the convenience store) should check on the toilet. A user may enter and exit through the door 148 without flushing the toilet in situations such as when the toilet is too dirty for use, when the toilet is not working, or both. The computer system 102 may identify these aforementioned situations based on calculating that ratio and comparing the ratio to a threshold ratio set by the entity.

The computer system 102 may determine a ratio of the determined number of the plurality of instances of the decrease in the level of water 120 to a number of instances wherein the door 148 changes from the first position to the second position based on the stored door information 152. In embodiments, the determined ratio may be compared to a stored threshold ratio. The stored threshold ratio may take into account situations wherein a user enters the bathroom 124 to use a sink or mirror instead of the toilet. The computer system 102 may then transmit the alert 118 to the user device 104 when the determined ratio is less than the threshold ratio. In these examples, the threshold ratio may be associated with the door 148 being an entryway into and out of the bathroom 124, an entryway into and out of an individual stall within the bathroom 124, or a combination thereof. In an example, the computer system 102 may determine that a toilet has flushed six times and the door 148 has opened and closed ten times during a period of two hours. In this example, the stored threshold ratio may be set at 7:10. The alert 118 may indicate that the determined ratio of 6:10 is less than the threshold ratio of 7:10 within a period of time and prompt an event, such as cleaning the toilet associated with the toilet tank 122 and/or maintenance of the toilet. This example may indicate that the toilet was dirty, unusable, not operating, or a combination thereof.

Example Automatic Alerting System for Determining an Ambient Concentration of Compositions for Bathroom Cleaning The automatic alerting system 100 may be implemented to determine volatile organic compounds (VOCs) within the ambient environment of the bathroom 124 in order to monitor cleaning of the bathroom 124. For example, the entity managing the bathroom 124 (i.e., the convenience store) may have a schedule for cleaning the bathroom 124, such as once per twelve hours. Someone associated with the entity, such as an employee, may be too busy performing other tasks to comply with the cleaning schedule. To monitor the cleaning of the bathroom 124 for compliance, the automatic alerting system 100 may register an event associated with cleaning the bathroom 124 based on different threshold values for various cleaning solutions. However, the employee may forget to clean the bathroom 124, may spill chemicals in an attempt to clean the bathroom 124, perform a cursory cleaning, or try to deceive the system 100 in order to perform other tasks.

In one or more embodiments, the automatic alerting system 100 may generate the alert 118 based, at least partly on, concentration measurements 160 of potential volatile organic compounds (VOCs) present in the bathroom 124. The alert 118 may be generated based solely or partly on the concentration measurements 160. For example, the sensor 108b may be disposed proximate to an exhaust fan 162 operable to receive an airflow from the exhaust fan 162. The exhaust fan 162 may direct air out from the bathroom 124. The sensor 108b may determine a concentration of one or more VOCs within the airflow received from the exhaust fan 162.

Sensor 108b is any appropriate device for sensing or measuring a concentration of one or more compounds, such as VOCs. For example, sensor 108b may be a VOC sensor that utilizes a light to ionize one or more molecules received by electrodes in order to measure a concentration of the one or more compounds. Without limitations, the sensor 108b may be a photoionization detector, a flame ionization detector, a metal oxide semiconductor sensor, or a combination thereof. Sensor 108b may include a light source 164, a pair of electrodes 166, and a sensor processor 168. In a particular embodiment, the light source 164 may produce a light (for example, ultraviolet light) configured to ionize one or more molecules of the VOC present in the airflow. The pair of electrodes 166 may receive the ionized one or more molecules and to generate an electrical current proportional to a concentration of the received, ionized one or more molecules. In one or more embodiments, the sensor processor 168 may be communicatively coupled to the light source 164 and the pair of electrodes 166. The sensor processor 168 may determine a concentration measurement 160 for the VOC based at least in part upon the electrical current generated by the pair of electrodes 166. The sensor processor 168 may further transmit each concentration measurement 160 across the network 106. In certain embodiments, sensor 108b may be communicatively coupled to a gateway 138, wherein the gateway 138 may send the concentration measurement 160 to computer system 102 via network 106.

In general, sensor 108b provides the concentration measurement 160 to computer system 102. Concentration measurement 160 may comprise any appropriate concentration value (e.g., parts per million). In some embodiments, concentration measurement 160 is provided automatically by sensor 108b at periodic intervals (e.g., every five minutes). In other embodiments, concentration measurement 160 is provided by sensor 108b when requested by computer system 102.

The computer system 102 may receive a concentration measurement 160 from the sensor 108b within a period of time. During operations, computer system 102 may compare the received concentration measurement 160 to a first threshold associated with an event of cleaning the bathroom 124. In embodiments, if the received concentration measurement 160 is not greater than the first threshold, the system 100 may continue to operate within the period of time by iteratively determining concentration measurements 160 and comparing the concentration measurements 160 to the first threshold. If there is a transition from the current period of time to a subsequent period of time, the computer system 102 may generate and transmit the alert 118 to the user device 104 indicating that the bathroom 124 was not cleaned within the previous period of time.

For example, the sensor 108b may monitor for concentrations of ammonia and ethanol. In this example, ammonia or ethanol may be present in aerosolized or spray cleaner solutions, in cleaner solutions for application on the floor and/or tiles of the bathroom 124, in a toilet associated with the toilet tank 122, and any combination thereof. Further, a particular cleaning solution may be comprised of any suitable volumetric concentration of ammonia. For example, one cleaning solution may comprise of 0.1%, 0.2%, or 0.3% ammonia. The computer system 102 may store different values for the first threshold based on different compounds. A first threshold for ammonia may comprise sub-thresholds, wherein each sub-threshold is associated with a particular cleaning solution. For example, a first sub-threshold for ammonia present in aerosolized or spray cleaner solutions may be within a range of about 0.5 parts per million (ppm) to about 3 ppm. A second sub-threshold for ammonia present in cleaner solutions comprising 0.1% ammonia may be within a range of about 16 ppm to about 28 ppm. A third sub-threshold for ammonia present in cleaner solutions comprising 0.2% ammonia may be within a range of about 36 ppm to about 90 ppm. A fourth sub-threshold for ammonia present in cleaner solutions comprising 0.3% ammonia may be within a range of about 125 ppm to about 150 ppm. With reference to ethanol, a first threshold may be within a range of about 0.5 ppm to about 50 ppm.

The computer system 102 may be further operable to compare the concentration measurement 160 to a second threshold if the concentration measurement 160 is determined to be greater than the first threshold. For example, the second threshold for ammonia and ethanol may be about 150 ppm. In certain embodiments, the second threshold is indicative of either an event of a spill of one or more chemicals occurring within the bathroom 124 or with an event of tampering of the sensor 108b. As the first threshold has already been surpassed by the concentration measurement 160 to indicate that the bathroom 124 has been cleaned, an increasing value of the concentration measurements 160 may indicate further production of one or more compounds, such as VOCs, in the bathroom 124. In an example event of a spill, one or more chemicals may continue to produce one or more compounds until cleaned and removed from the bathroom. In an example event of tampering with the sensor 108b, an employee associated with the entity may continue to produce one or more compounds by spraying an aerosolized compound towards the sensor 108 for a period of time.

To distinguish between events, the computer system 102 may determine a moving average of a concentration of one or more compounds, such as VOCs, present in the airflow over a given time period (for example, 10 minutes). The moving average is representative of the average concentration of one or more compounds within a rolling window of time over the period of time. The moving average may smooth out short-term fluctuations in the concentration measurements and highlight longer-term trends. In embodiments, the moving average may be simple, cumulative, exponential, weighted, or any combination thereof. For example, the rolling window of time may be designated for 2 minutes for an overall period of time of 10 minutes. In this example, the computer system 102 may determine the following concentrations of ammonia: 125 ppm at 15 seconds, 125 ppm at 30 seconds, 127 ppm at 45 seconds, 135 ppm at 60 seconds, 135 ppm at 75 seconds, 135 ppm at 90 seconds, 130 ppm at 105 seconds, 135 ppm at 120 seconds, 140 ppm at 135 seconds, and 145 ppm at 150 seconds. The average concentration of ammonia within the rolling window of time for the initial two minutes of operation is 130.875 ppm (i.e., average of the first eight concentration measurements). As time increases, the computer system 102 may adjust the average concentration to include newer concentration measurements. For example, at a time of 135 seconds, the rolling window may shift from 0-120 seconds to 15-135 seconds to maintain a rolling window of time of two minutes. The average concentration of ammonia within the updated rolling window of time is 132.75 ppm (i.e., average of the concentration measurements taken from 15-135 seconds).

The computer system 102 may then compare the determined moving average to the second threshold. If the determined moving average comprises an average concentration that is less than the second threshold, the computer system 102 may generate and transmit the alert 118 to the user device 104 indicating that the sensor 108b has been tampered. The average concentration being less than the second threshold is indicative of a temporary increase in concentration for a given VOC. In an example, the concentration of ammonia may increase to 160 ppm within a period of thirty seconds. As the exhaust fan 162 operates to remove airflow containing one or more compounds, the concentration of ammonia may decrease to 100 ppm within the next minute and may remain at that value. The computer system 102 may associate this temporary increase past the second threshold (i.e., 150 ppm) and subsequent decrease to a constant value as an event of tampering with the sensor 108b (for example, by spraying an aerosolized compound proximate to the sensor 108b). If the determined moving average comprises an average concentration that is greater than the second threshold, the computer system 102 may generate and transmit the alert 118 to the user device 104 indicating that an event associated with a spill of one or more chemicals has occurred within the bathroom 124. In another example, the concentration of ammonia may steadily increase past a second threshold of 150 ppm. The concentration of ammonia may maintain a value over the second threshold for an amount of time (for example, the rolling window), despite operation of the exhaust fan 162. The computer system 102 may associate this increase past the second threshold and maintenance above the second threshold as an event associated with a spill of one or more chemicals.

In an example, a user may attempt to tamper with the sensor 108b by spraying an aerosolized compound proximate to the sensor 108b. The user may spray an aerosolized compound proximate to the sensor 108b in order to register a false positive that there is a concentration of one or more compounds greater than the first threshold. In this example, the user may attempt to comply with a determined cleaning schedule for the bathroom 124 without performing the actions of cleaning the bathroom 124. For example, the user may be busy performing other tasks but is aware that the bathroom 124 needs cleaning. A directed spraying of the aerosolized compound towards the sensor 108b may overcome the first threshold to signal that the bathroom 124 has been cleaned, but too much of the aerosolized compound may exceed the second threshold.

The aerosolized compound may be present within the bathroom 124 for a certain duration of time before the airflow through the exhaust fan 162 may remove the one or more molecules of the aerosolized compound. In this example, the sensor 108b may monitor an increase in the concentration of the aerosolized compound by iteratively determining concentration measurements 160. The computer system 102 may receive a concentration measurement 160 exceeding the second threshold before the one or more molecules of the aerosolized compound are removed from the bathroom 124. Depending on the duration of time present in the bathroom 124, the concentration of the aerosolized compound may be insignificant or negligible. The longer the duration of time the aerosolized compound is present in the bathroom 124, the greater an increase of the moving average of concentration measurements of the aerosolized compound will be.

For example, in an event associated with a spill of one or more chemicals occurring in the bathroom 124, a larger release of one or more compounds may occur when compared to spraying an aerosolized compound. Depending on a variety of factors, such as volume of the liquid of the one or more chemicals spilled, temperature within the bathroom 124, ventilation, duration of time exposed to the environment within the bathroom, the spilled one or more chemicals may produce one or more compounds at a certain rate. In this example, the rate of production may be greater when the temperature is high, when there is poor ventilation, when there is a large duration of time, or a combination thereof. The computer system 102 may detect an increase in concentration of the produced one or more compounds based on the concentration measurements 160 determined by the sensor 108b. As the duration of time wherein the spilled one or more chemicals is exposed may be large, the moving average of the concentration of those produced one or more compounds may increase in relation.

For example, a moving average for one or more compounds determined before the spill may be 100 ppm, wherein this may signify that the average concentration of the one or more compounds is 100 ppm for the rolling window. After the spill, the one or more chemicals may not be removed or cleaned by the user wherein during that time period, one or more compounds, such as VOCs, may be produced. A moving average determined after the spill may increase to 151 ppm. If the second threshold is 150 ppm, the computer system 102 may generate and transmit the alert 118 to the user device 104 indicating that an event associated with a spill of one or more chemicals has occurred within the bathroom 124 as the moving average comprises an average concentration greater than 150 ppm. In this example, the alert 118 may prompt an event, such as cleaning spilled one or more chemicals, venting the produced VOCs out through the exhaust fan 162, or both.

In another example, the computer system 102 determines that the user tampered with the sensor 108b. In this example, the computer system 102 determines that the moving average comprises an average concentration that is less than the second threshold. The alert 118 generated and transmitted by the computer system 102 may indicate that the sensor 108*b* has been tampered and prompt an event, such as cleaning the bathroom 124 and/or inspecting the sensor 108*b*.

In a separate example, the user may not have cleaned the bathroom 124 according to the schedule (i.e., once per twelve hours). When the computer system 102 determines that there has not been a cleaning within the schedule, the alert 118 generated and transmitted may indicate that the bathroom 124 was not cleaned within a given period of time and prompt an event, such as cleaning the bathroom 124. In these examples, the alert 118 may be generated and transmitted via the automatic alerting module 114 of the computer system 102.

As previously described, automatic alerting module 114 represents any suitable set of instructions, logic, or code embodied in a computer-readable storage medium. For example, automatic alerting module 114 may be embodied in memory 110, a disk, a CD, or a flash drive. In particular embodiments, automatic alerting module 114 may include alerting instructions 142 (e.g., a software application) executable by processor 112 to perform one or more of the functions described herein. In general, automatic alerting module 114 sends alert 118 for display on user device 104 via network 106. As described, alert 118 is generated by alerting instructions 142 based, at least in part, on the concentration measurements 160 from sensor 108*b* and on threshold values determined via the thresholding module 116.

Thresholding module 116 represents any suitable set of instructions, logic, or code embodied in a computer-readable storage medium. For example, thresholding module 116 may be embodied in memory 110, a disk, a CD, or a flash drive. In particular embodiments, thresholding module 116 may include thresholding instructions 140 (e.g., a software application) executable by processor 112 to perform one or more of the functions described herein. In general, thresholding instructions 140 determine a first threshold and a second threshold for a period of time. For example, the first threshold represents an event indicating that the bathroom 124 has been cleaned, and the second threshold represents an event indicating either a spill of chemicals in the bathroom or an event of tampering with sensor 108*b*. Each value for first and second thresholds may be any suitable value (for example, 75 ppm, 125 ppm, 150 ppm, etc.). As described above, the first threshold is compared to each received concentration measurements 160. The second threshold is then compared to each received concentration measurements 160 and to a determined moving average.

Figure 2:
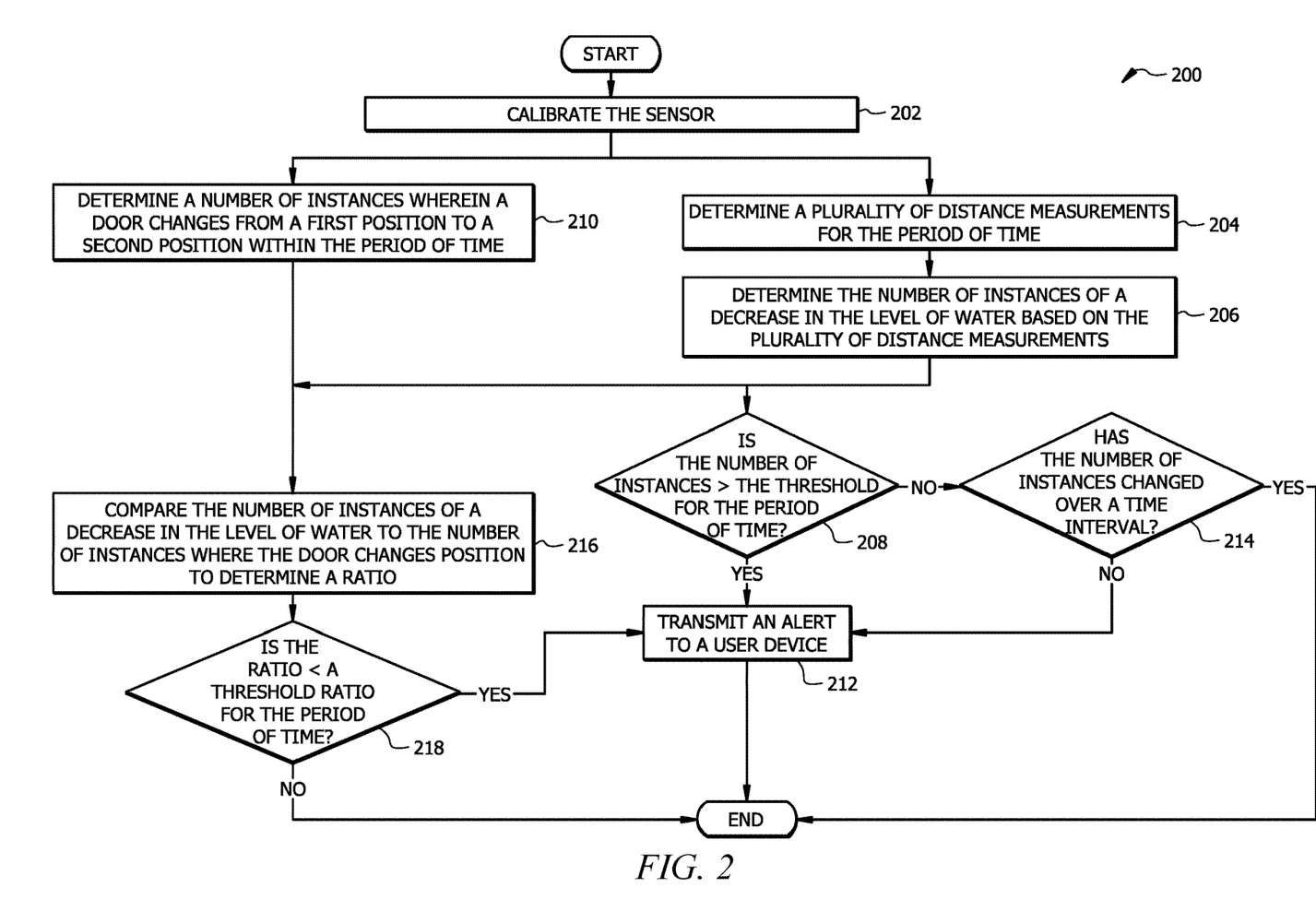
FIG. 2 is a flow diagram illustrating a first example operation of the alerting system of FIG. 1.

Example Operation of the System for Diagnostic Analysis of a Toilet Over Time Intervals FIG. 2 is a flow diagram illustrating an example method 200 of the automatic alerting system 100 of FIG. 1. In general, method 200 may be utilized by the sensor 108*a*, switch 144, computer system 102, and user device 104 of FIG. 1 to automatically provide the alert 118 for display on user device 104. The method 200 may begin at operation 202 where the sensor 108*a* (referring to FIG. 1) may be calibrated relative to the toilet tank 122 (referring to FIG. 1). The sensor 108*a* may perform a first distance measurement 126*a* (referring to FIG. 1) to determine a distance from the level of water 120 (referring to FIG. 1) contained in the toilet tank 122 to the sensor 108*a* at an initial water level. The sensor 108*a* may then transmit the first distance measurement 126*a* to the computer system 102 across the network 106 (referring to FIG. 1). The processor 112 (referring to FIG. 1) of the computer system 102 may receive the transmitted first distance measurement 126*a* from the network 106 and may instruct the memory 110 (referring to FIG. 1) to store the first distance measurement 126*a* as the setpoint 128 (referring to FIG. 1). The method 200 may then proceed to both operation 204 and to operation 206 for parallel operations.

At operation 204, the sensor 108*a* may determine a plurality of distance measurements 126 for a period of time (i.e., eight hours). For each distance measurement 126, the laser diode 130 (referring to FIG. 1) of the sensor 108*a* may produce the laser beam 136 that travels towards the level of water 120, wherein the laser beam 136 is reflected off of the water 120 to travel back to the sensor 108*a*. The photodetector 132 (referring to FIG. 1) of the sensor 108*a* may receive the reflected laser beam 136. The sensor processor 134 (referring to FIG. 1) of the sensor 108*a* may determine each distance measurement 126 based on a difference in time between production of the laser beam 136 by the laser diode 130 and reception of the reflected laser beam 136 by the photodetector 132. The sensor processor 134 may further transmit the plurality of distance measurements 126 across the network 106.

At operation 208, the processor 112 of the computer system 102 may receive the plurality of distance measurements 126 transmitted over the network 106. The processor 112 of the computer system 102 may then determine a plurality of instances of a decrease in the level of water 120 (for example, an event associated with flushing the toilet tank 122) based on a comparison between each one of the received distance measurements 126 and the setpoint 128. The method 200 may then proceed to operation 210 and to operation 212 concurrently.

At operation 210, the processor 112 of the computer system 102 may determine whether the determined plurality of instances of the decrease in the level of water 120 is greater than the threshold number stored in the memory 110 for the period of time. If there is a determination that the determined plurality of instances of the decrease in the level of water 120 is greater than the threshold number, the method 200 proceeds to operation 214. Otherwise, the method 200 proceeds to operation 216.

At operation 214, the processor 112 of the computer system 102 may transmit the alert 118 across the network 106 to the user device 104. The alert 118 may indicate that the determined plurality of instances of the decrease in the level of water 120 is greater than the threshold number. Transmission of the alert 118 may signal for an event to occur, such as cleaning the toilet associated with the toilet tank 122. After transmission of the alert 118, the method 200 proceeds to end.

At operation 216, the processor 112 of the computer system 102 may determine whether there has been a change in the determined number of the plurality of instances of the decrease in the level of water 120 over a time interval (for example, two hours). If there is a determination that the determined number of the plurality of instances of the decrease in the level of water 120 has not changed over the time interval, the method 200 proceeds to operation 214. Otherwise, the method 200 proceeds to end. As previously described, the processor 112 of the computer system 102 may transmit the alert 118 across the network 106 to the user device 104 in operation 214. In this embodiment, transmission of the alert 118 may signal for an event to occur, such as cleaning the toilet and/or performing maintenance on the toilet associated with the toilet tank 122. After transmission of the alert 118, the method 200 proceeds to end.

Referring back to operation 206, the switch 144 (referring to FIG. 1) may determine an instance of transition from the closed position to the open position of the pair of contacts 154 (referring to FIG. 1). The pair of contacts 154 may be in a closed position when in proximity to the magnet 158 (referring to FIG. 1) coupled to the door 148 (referring to FIG. 1), wherein the pair of contacts 154 transitions from the closed position to the open position as the door 148 changes from the first position to the second position (for example, by rotating along a side of the door frame 146). The switch processor 156 (referring to FIG. 1) may determine an instance of transition from the closed position to the open position and transmit each instance of transition across the network 106. The processor 112 of the computer system 102 may receive each instance of transition and count each received instance of transition for the pair of contacts within the period of time for storage as the door information 152 (referring to FIG. 1).

At operation 212, the processor 112 of the computer system 102 may determine a ratio of the determined number of the plurality of instances of the decrease in the level of water 120 from operation 208 to a number of instances wherein the door 148 changes from the first position to the second position based on the stored door information 152 from operation 206. In embodiments, the determined ratio may then be compared to a stored threshold ratio.

At operation 218, the processor 112 of the computer system 102 may determine whether the determined ratio is greater than the stored threshold ratio. If there is a determination that the determined ratio is greater than the stored threshold ratio, the method 200 proceeds to end. Otherwise, the method 200 proceeds back to operation 214. As previously described, the processor 112 of the computer system 102 may transmit the alert 118 across the network 106 to the user device 104 in operation 214. In this embodiment, transmission of the alert 118 may signal for an event to occur, such as cleaning the toilet associated with the toilet tank 122 and/or the bathroom 124. After transmission of the alert 118, the method 200 proceeds to end.

Figure 3:
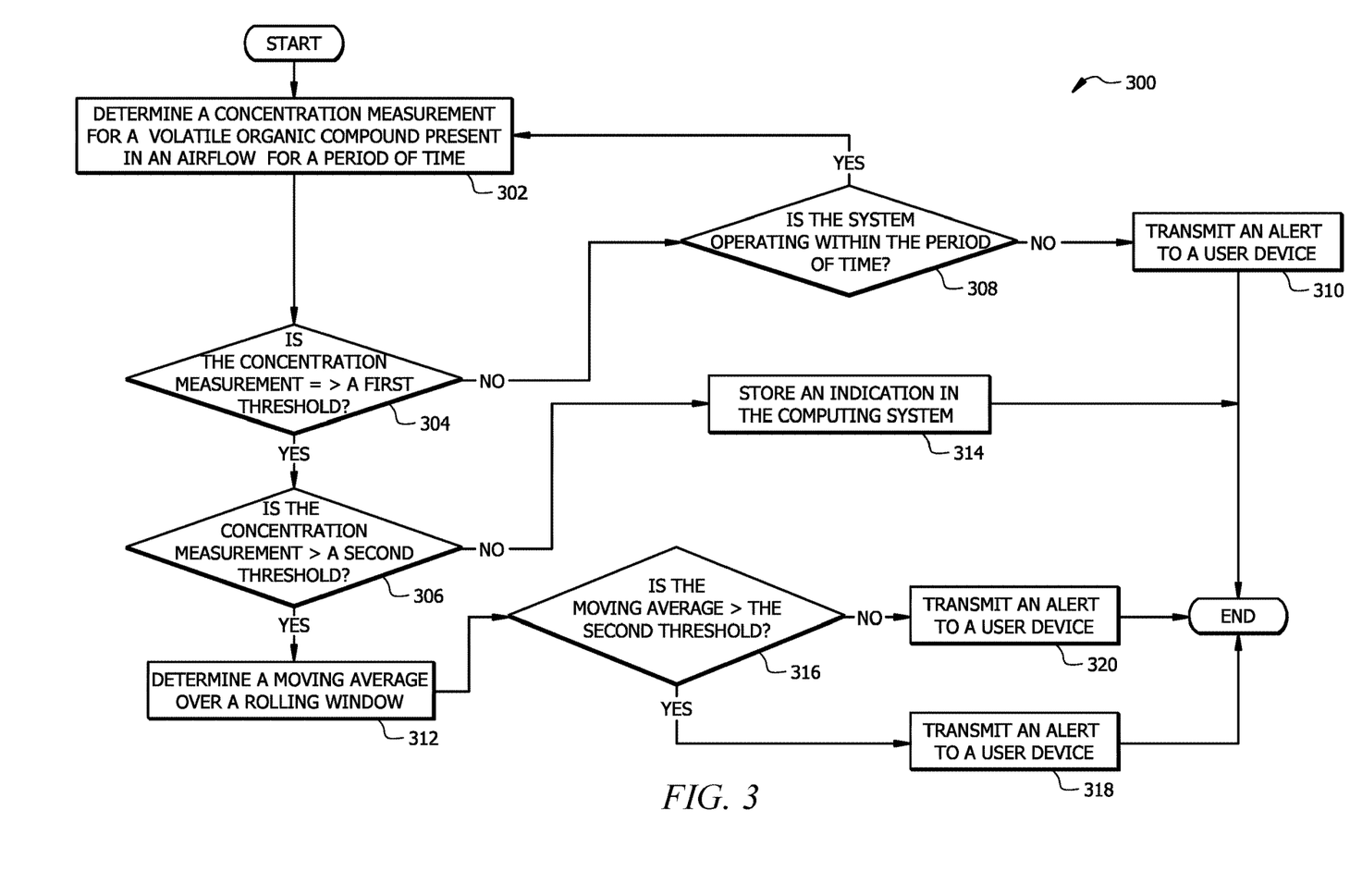
FIG. 3 is a flow diagram illustrating a second example operation of the alerting system of FIG. 1.

Example Operation of the System for Determining an Ambient Concentration of Compositions for Bathroom Cleaning FIG. 3 is a flow diagram illustrating an example method 300 of the automatic alerting system 100 of FIG. 1. In general, method 300 may be utilized by the sensor 108*b*, computer system 102, and user device 104 of FIG. 1 to automatically provide the alert 118 for display on user device 104. The method 300 may begin at operation 302 where the sensor 108*b* (referring to FIG. 1) may be determine a concentration measurement 160 for one or more compounds, such as VOCs, present in the airflow for a period of time. The light source 164 (referring to FIG. 1) may produce a light (for example, ultraviolet light) configured to ionize one or more molecules of the VOC present in the airflow. The pair of electrodes 166 (referring to FIG. 1) may receive the ionized one or more molecules and generate an electrical current proportional to a concentration of the received, ionized one or more molecules. The sensor processor 168 (referring to FIG. 1) may determine a concentration measurement 160 for the VOC based at least in part upon the electrical current generated by the pair of electrodes 166. The sensor processor 168 may further transmit the concentration measurement 160 across the network 106.

At operation 304, the processor 112 (referring to FIG. 1) of the computer system 102 may receive the concentration measurement 160 transmitted over the network 106.

The processor 112 of the computer system 102 may then determine whether the received concentration measurement 160 is greater than or equal to a first threshold stored in the memory 110 (referring to FIG. 1) during the period of time. The first threshold is indicative of an event associated with cleaning the bathroom 124 (referring to FIG. 1). If the received concentration measurement 160 is greater than or equal to the first threshold, the computer system 102 determines that a user has cleaned the bathroom 124. If there is a determination that the received concentration measurement 160 is greater than or equal to the first threshold, the method 300 proceeds to operation 306. Otherwise, the method 300 proceeds to operation 308.

At operation 308, the processor 112 of the computer system 102 may determine whether the system 100 is operating within a first period of time. For example, an entity managing the bathroom 124 may monitor cleaning of the bathroom 124 through a schedule (i.e., once per twelve hours). In this example, the first period of time may be a twelve-hour shift from 8 AM to 8 PM. During operation 308, the computer system 102 may determine if the system 100 is still operating within the twelve-hour shift or past the twelve-hour shift (i.e., past 8:01 PM). If there is a determination that the system 100 is operating within the first period of time, the method 300 proceeds to back to operation 302. The system 100 may repeat operation 302, operation 304, and operation 308 to iteratively determine concentration measurements 160 and compare the determined concentration measurements 160 to the first threshold while operating within the first period of time. For example, the computer system 102 may continue to monitor the concentration of VOCs either until the first threshold is exceeded (potentially indicating that the bathroom has been cleaned) or until the twelve-hour shift has ended. Otherwise, the method 300 proceeds to operation 310.

At operation 310, the processor 112 of the computer system 102 may transmit the alert 118 across the network 106 to the user device 104. In this example, the period of time in which the entity was to clean the bathroom 124 has passed (i.e., based on the cleaning schedule). The bathroom 124 may have required a cleaning once every twelve hours. After the end of the twelfth hour, if there was no determined cleaning based on a comparison between the received concentration measurement 160 and the first threshold, the computer system 102 generates the alert 118. The alert 118 may indicate that the bathroom 124 was not cleaned within a given period of time (i.e., the first period of time). Transmission of the alert 118 may signal for an event to occur, such as cleaning the bathroom 124. After transmission of the alert 118, the method 300 proceeds to end.

Referring back to operation 306, the processor 112 of the computer system 102 may determine whether the received concentration measurement 160 is greater than a second threshold stored in the memory 136. The second threshold is indicative of further production of VOCs not typical of an event of cleaning the bathroom 124. Such events may include spilling one or more chemicals in the bathroom 124 or tampering with the sensor 108*b*. If there is a determination that the received concentration measurement 160 is greater than the second threshold, the method 300 proceeds to operation 312. For example, one received concentration measurement 160 may comprise a value of 149 ppm, and the second threshold may be 150 ppm. Another received concentration measurement 160 may comprise a value of 155 ppm, thereby exceeding the second threshold. The increasing value of concentration measurements 160 indicates further production of VOCs in the bathroom 124 (for example, from a spill or from tampering with the sensor 108b). Otherwise, the method 300 proceeds to operation 314.

At operation 314, the processor 112 of the computer system 102 may determine that the entity managing the bathroom 124 has complied with the cleaning schedule. For example, an employee for the entity may have cleaned the bathroom 124 within the twelve-hour shift. After the cleaning, the processor 112 of the computer system 102 may have determined for the received concentration measurement 160 to comprise a value between the first threshold and the second threshold. The processor 112 may instruct the memory 110 to store an indication that the bathroom 124 was cleaned in response to a determination that the received concentration measurement 160 is greater than the first threshold and less than the second threshold. After storing the indication, the method 300 proceeds to end.

Referring back to operation 312, the processor 112 of the computer system 102 may determine a moving average of an average concentration of one or more compounds present in the airflow over a given time period (for example, 10 minutes). The moving average is representative of the average concentration of one or more compounds within a rolling window of time over the period of time. Determining the moving average may distinguish between individual false positive indications of cleaning the bathroom 124 (i.e., a spill or tampering with the sensor 108b). In an example event of a spill, one or more chemicals may continue to produce one or more compounds, such as VOCs, until cleaned and removed from the bathroom 124. In an example event of tampering with the sensor 108b, an employee associated with the entity may continue to produce one or more VOCs by spraying an aerosolized compound towards the sensor 108 for a period of time.

At operation 316, the processor 112 of the computer system 102 may then compare the determined moving average to the second threshold to determine whether the determined moving average comprises an average concentration that is greater than the second threshold. The determined moving average being less than the second threshold is indicative of a temporary increase in concentration for a given VOC. In an example, the concentration of ammonia may increase to 160 ppm within a period of thirty seconds. As the exhaust fan 162 operates to remove airflow containing one or more compounds, the concentration of ammonia may decrease to 100 ppm within the next minute and may remain at that value. The computer system 102 may associate this temporary increase past the second threshold (i.e., 150 ppm) and subsequent decrease to a constant value as an event of tampering with the sensor 108b (for example, by spraying an aerosolized compound proximate to the sensor 108b). If there is a determination that the determined moving average is greater than the second threshold, the method 300 proceeds to operation 318. In another example, the concentration of ammonia may steadily increase past a second threshold of 150 ppm. The concentration of ammonia may maintain a value over the second threshold for an amount of time, despite operation of the exhaust fan 162. The computer system 102 may associate this increase past the second threshold and maintenance above the second threshold as an event associated with a spill of one or more chemicals. Otherwise, the method 300 proceeds to operation 320.

At both operation 318 and operation 320, the processor 112 of the computer system 102 may transmit the alert 118 across the network 106 to the user device 104. With reference to operation 318, the alert 118 may indicate that an event associated with a spill of one or more chemicals has occurred within the bathroom 124. Transmission of the alert 118 may signal for an event to occur, such as cleaning or removing the spill in the bathroom 124. With reference to operation 320, the alert 118 may indicate that the sensor 108 has been tampered. Transmission of the alert 118 may signal for an event to occur, such as inspecting the sensor 108b. After transmission of the alert 118, the method 300 proceeds to end.

Modifications, additions, or omissions may be made to the methods described herein without departing from the scope of the disclosure. The methods may include more, fewer, or other steps. Additionally, steps may be performed in any suitable order. That is, the steps of any method disclosed herein do not have to be performed in the exact order disclosed, unless explicitly stated.

As used in this document, "each" refers to each member of a set or each member of a subset of a set. Furthermore, as used in the document "or" is not necessarily exclusive and, unless expressly indicated otherwise, can be inclusive in certain embodiments and can be understood to mean "and/or." Similarly, as used in this document "and" is not necessarily inclusive and, unless expressly indicated otherwise, can be inclusive in certain embodiments and can be understood to mean "and/or." All references to "a/an/the element, apparatus, component, means, step, etc." are to be interpreted openly as referring to at least one instance of the element, apparatus, component, means, step, etc., unless explicitly stated otherwise.

Furthermore, reference to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

The embodiments disclosed herein are only examples, and the scope of this disclosure is not limited to them. Particular embodiments may include all, some, or none of the components, elements, features, functions, operations, or steps of the embodiments disclosed herein. Certain embodiments are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

What is claimed is:

1. A system for determining an ambient concentration of a volatile organic compound comprising:
a sensor disposed proximate to an exhaust fan operable to receive an airflow from the exhaust fan, the sensor comprising:
a light source operable to produce a light configured to ionize one or more molecules of the volatile organic compound present in the airflow;
a pair of electrodes operable to:
receive the ionized one or more molecules; and
generate an electrical current proportional to a concentration of the ionized one or more molecules; and
a first processor communicatively coupled to the pair of electrodes, configured to:
determine a concentration measurement for the volatile organic compound based at least in part upon the electrical current generated by the pair of electrodes; and
transmit the concentration measurement across a network; and
a computer system communicatively coupled to the sensor, comprising:
a memory operable to:
store a first threshold for the concentration measurement associated with an event of cleaning a bathroom;
store a second threshold for the concentration measurement, wherein the second threshold is greater than the first threshold; and
a second processor operably coupled to the memory, configured to:
receive the concentration measurement from the network within a first period of time;
compare the received concentration measurement to the first threshold;
compare the received concentration measurement to the second threshold; and
instruct the memory to store an indication that the bathroom was cleaned in response to a determination that the received concentration measurement is greater than the first threshold and less than the second threshold.

2. The system of claim 1, wherein the second processor is further configured to:
determine a moving average of the concentration of the volatile organic compound in the airflow in response to a determination that the received concentration measurement is greater than the second threshold;
compare the determined moving average to the second threshold; and
send an alert for display on a user device indicating that an event associated with a spill of one or more chemicals has occurred in the bathroom in response to a determination that the determined moving average is greater than the second threshold.

3. The system of claim 2, wherein the second processor is further configured to:
send an alert for display on the user device indicating that the sensor has been tampered with in response to a determination that the determined moving average is less than the second threshold.

4. The system of claim 1, wherein the second processor is further configured to:
determine that the system is operating within a subsequent period of time in response to a determination that the received concentration measurement is not greater than the first threshold; and
send an alert for display on a user device indicating that the bathroom was not cleaned within the first period of time.

5. The system of claim 1, wherein the second processor is further configured to:
verify that the system is operating within the first period of time in response to a determination that the received concentration measurement is not greater than the first threshold;
receive a subsequent concentration measurement from the network; and
compare the subsequent concentration measurement to the first threshold and to the second threshold.

6. The system of claim 5, wherein the second processor is further configured to:
determine that the subsequent concentration measurement is greater than the first threshold and less than the second threshold; and
instruct the memory to store an indication that the bathroom was cleaned within the first period of time.

7. The system of claim 1, wherein:
the first processor is further configured to transmit the concentration measurement via a gateway using an Internet-of-Things communications protocol; and
the gateway is operable to transmit the concentration measurement to the computer system.

8. A method for determining an ambient concentration of a volatile organic compound comprising:
receiving a concentration measurement from a sensor across a network within a first period of time;
comparing the received concentration measurement to a first threshold;
comparing the received concentration measurement to a second threshold, wherein the second threshold is greater than the first threshold; and
storing an indication that a bathroom was cleaned in response to a determination that the received concentration measurement is greater than the first threshold and less than the second threshold.

9. The method of claim 8, further comprising:
determining a moving average of the concentration of the one or more molecules of the volatile organic compound in the airflow in response to a determination that the received concentration measurement is greater than the second threshold;
comparing the determined moving average to the second threshold; and
sending an alert for display on a user device indicating that an event associated with a spill of one or more chemicals has occurred in the bathroom in response to a determination that the determined moving average is greater than the second threshold.

10. The method of claim 9, further comprising:
sending an alert for display on the user device indicating that the sensor has been tampered with in response to a determination that the determined moving average is less than the second threshold.

11. The method of claim 8, further comprising:
determining that the system is operating within a subsequent period of time in response to a determination that the received concentration measurement is not greater than the first threshold; and sending an alert for display on a user device indicating that the bathroom was not cleaned within the first period of time.

12. The method of claim 8, further comprising:
verifying that the system is operating within the first period of time in response to a determination that the received concentration measurement is not greater than the first threshold;
receiving a subsequent concentration measurement from the network; and
comparing the subsequent concentration measurement to the first threshold and to the second threshold.

13. The method of claim 12, further comprising:
determining that the subsequent concentration measurement is greater than the first threshold and less than the second threshold; and
storing an indication that the bathroom was cleaned within the first period of time.

14. The method of claim 8, wherein the sensor is configured to transmit the concentration measurement via a gateway using an Internet-of-Things communications protocol.

15. A non-transitory computer-readable medium storing instructions that, when executed by a processor, cause the processor to:
receive a concentration measurement from a sensor across a network within a first period of time;
compare the received concentration measurement to a first threshold;
compare the received concentration measurement to a second threshold, wherein the second threshold is greater than the first threshold; and
instruct a memory communicatively coupled to the processor to store an indication that a bathroom was cleaned in response to a determination that the received concentration measurement is greater than the first threshold and less than the second threshold.

16. The non-transitory computer-readable medium of claim 15, wherein the instructions are further configured to:
determine a moving average of the concentration of a volatile organic compound in an airflow in response to a determination that the received concentration measurement is greater than the second threshold;
compare the determined moving average to the second threshold; and
send an alert for display on a user device indicating that an event associated with a spill of one or more chemicals has occurred in the bathroom in response to a determination that the determined moving average is greater than the second threshold.

17. The non-transitory computer-readable medium of claim 16, wherein the instructions are further configured to:
send an alert for display on the user device indicating that the sensor has been tampered with in response to a determination that the determined moving average is less than the second threshold.

18. The non-transitory computer-readable medium of claim 15, wherein the instructions are further configured to:
determine that the system is operating within a subsequent period of time in response to a determination that the received concentration measurement is not greater than the first threshold; and
send an alert for display on a user device indicating that the bathroom was not cleaned within the first period of time.

19. The non-transitory computer-readable medium of claim 18, wherein the instructions are further configured to:
verify that the system is operating within the first period of time in response to a determination that the received concentration measurement is not greater than the first threshold;
receive a subsequent concentration measurement from the network; and
compare the subsequent concentration measurement to the first threshold and to the second threshold.

20. The non-transitory computer-readable medium of claim 15, wherein the instructions are further configured to:
receive the concentration measurement from the network via a gateway communicatively coupled to the sensor using an Internet-of-Things communications protocol.

* * * * *